United States Patent
Jacovini

(10) Patent No.: US 11,135,350 B2
(45) Date of Patent: Oct. 5, 2021

(54) CATHETER ANCHOR DRAIN

(71) Applicant: Stacey Jacovini, Philadelphia, PA (US)

(72) Inventor: Stacey Jacovini, Philadelphia, PA (US)

(*) Notice: Subject to any disclaimer, the term of this patent is extended or adjusted under 35 U.S.C. 154(b) by 35 days.

(21) Appl. No.: 15/007,886

(22) Filed: Jan. 27, 2016

(65) Prior Publication Data
US 2016/0213887 A1 Jul. 28, 2016

Related U.S. Application Data

(60) Provisional application No. 62/108,123, filed on Jan. 27, 2015.

(51) Int. Cl.
*A61M 1/00* (2006.01)
*A61M 25/00* (2006.01)
*A61M 27/00* (2006.01)

(52) U.S. Cl.
CPC .............. *A61M 1/86* (2021.05); *A61M 25/00* (2013.01); *A61M 27/00* (2013.01); *A61M 2025/0008* (2013.01)

(58) Field of Classification Search
CPC ........ A61M 1/0086; A61M 2025/0008; A61M 25/00; A61M 25/02; A61M 27/00; A61M 2025/0286; A61M 1/0039; A61M 1/0058; A61M 1/0064; A61M 1/008; A61M 1/0088
See application file for complete search history.

(56) References Cited

U.S. PATENT DOCUMENTS

| | | | | |
|---|---|---|---|---|
| 3,823,720 A * | 7/1974 | Tribble | ............... | A61M 1/0084 604/43 |
| 4,500,311 A * | 2/1985 | Redmond | ........... | A61M 27/006 600/581 |
| 4,552,553 A * | 11/1985 | Schulte | ............... | A61M 27/006 604/9 |
| 4,867,740 A * | 9/1989 | East | ..................... | A61M 27/006 604/9 |
| 5,387,188 A * | 2/1995 | Watson | ............... | A61M 27/006 604/10 |
| 5,391,159 A * | 2/1995 | Hirsch | ................. | A61J 15/0019 604/175 |
| 5,405,339 A * | 4/1995 | Kohnen | ................. | A61M 39/12 285/239 |
| 5,603,730 A * | 2/1997 | Romkee | ................. | A61N 1/057 604/175 |
| 5,746,722 A * | 5/1998 | Pohndorf | .............. | A61M 25/02 604/175 |
| 5,770,139 A * | 6/1998 | Kinghorn | .............. | A61M 39/12 264/230 |

(Continued)

*Primary Examiner* — Adam Marcetich
(74) *Attorney, Agent, or Firm* — Nanda P. B. A. Kumar; Law Offices of Nanda P.B.A. Kumar, LLC

(57) ABSTRACT

The disclosure relates to a system of circumferentially (preferably helically) arranging indicia on the elongate body of a medical device such as a catheter. The disclosure also relates to an anchor drain for securing a surgical drain to a fluid collection device. The anchor drain resists disconnection of the surgical drain from the fluid collection device and also resists occlusion of the conduit connecting the surgical drain and the fluid collection device, even when a suture is tied about a portion of the anchor drain inserted within the surgical drain, and resists unintentional withdrawal of the surgical drain from the body or a body cavity.

4 Claims, 6 Drawing Sheets

(56) References Cited

U.S. PATENT DOCUMENTS

| | | | | |
|---|---|---|---|---|
| 5,807,342 A * | 9/1998 | Musgrave | A61M 25/02 128/DIG. 26 |
| 5,913,852 A * | 6/1999 | Magram | A61M 27/002 604/284 |
| 6,003,906 A * | 12/1999 | Fogarty | A61M 39/12 285/242 |
| 6,286,179 B1 * | 9/2001 | Byrne | A61B 1/00119 134/169 C |
| 2002/0128588 A1 * | 9/2002 | Borgesen | A61M 27/006 604/9 |
| 2003/0105047 A1 * | 6/2003 | Kaemmerer | A61K 48/005 514/44 R |
| 2004/0044330 A1 * | 3/2004 | Li | A61M 39/0247 604/535 |
| 2004/0243103 A1 * | 12/2004 | King | A61M 25/0009 604/533 |
| 2005/0148913 A1 * | 7/2005 | Weston | A61M 1/0088 602/2 |
| 2006/0015040 A1 * | 1/2006 | Yunoki | A61M 25/09 600/585 |
| 2007/0260222 A1 * | 11/2007 | Kraus | A61M 25/0014 604/527 |
| 2008/0012299 A1 * | 1/2008 | Kidman | F16L 33/03 285/242 |
| 2008/0154326 A1 * | 6/2008 | Clyne | A61N 1/057 607/36 |
| 2008/0228174 A1 * | 9/2008 | Ibrahim | A61M 25/02 604/541 |
| 2008/0319398 A1 * | 12/2008 | Bizup | F16L 33/225 604/175 |
| 2008/0319421 A1 * | 12/2008 | Bizup | A61M 39/12 604/535 |
| 2011/0040257 A1 * | 2/2011 | Behymer | A61M 25/02 604/175 |
| 2012/0223517 A1 * | 9/2012 | Morrissey | F16L 33/34 285/125.1 |
| 2012/0274064 A1 * | 11/2012 | Moore | F16L 33/227 285/398 |
| 2013/0338599 A1 * | 12/2013 | Kaylor | A61M 27/002 604/175 |
| 2015/0112289 A1 * | 4/2015 | Stebbins | A61M 27/006 604/318 |
| 2016/0038724 A1 * | 2/2016 | Madsen | A61M 27/006 604/9 |
| 2017/0189655 A1 * | 7/2017 | Fabiano | A61M 39/1011 |
| 2017/0258981 A1 * | 9/2017 | Franano | A61M 1/3653 |
| 2017/0325685 A1 * | 11/2017 | Shachar | A61B 5/0031 |

\* cited by examiner

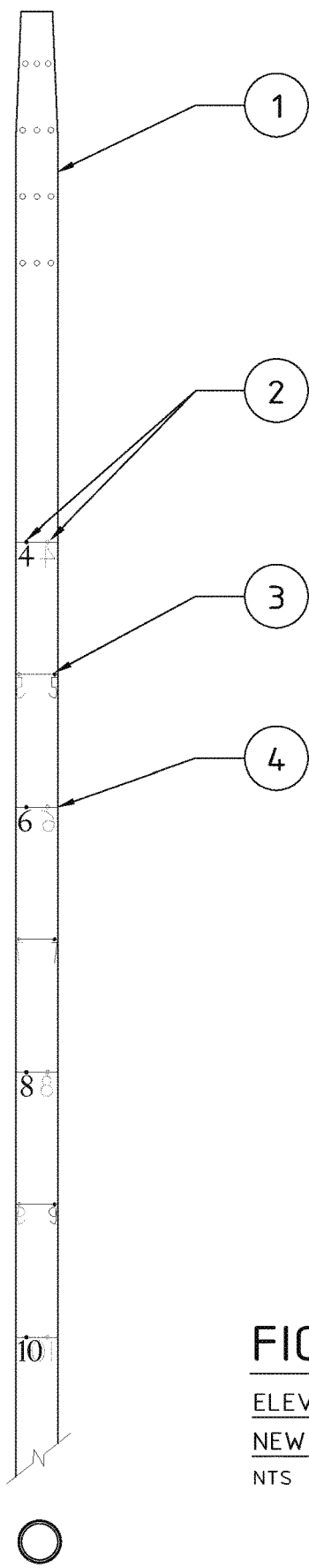

CATHETER CIRCUMFERENTIAL NUMBERING SYSTEM

1. EXISTING CATHETER DESIGN BY OTHERS (TIP, PERFORATIONS, ETC.)
2. INDICIA (#cm FROM TIP) TO BE EVERY CENTIMETER; EACH INDICIA TO BE PRINTED TWICE, ON OPPOSING FACES OF CATHETER/PROBE (= 180 deg FROM EACH OTHER)
3. EACH ADDITIONAL CENTIMETER, INDICIA LOCATION TO BE ROTATED 90deg
4. THERE WILL BE A SOLID LINE INTERSECTING THE "DOT" OF THE INDICIA AT EVERY CENTIMETER SO IT IS CLEAR WHAT THE MARK REGISTERS/WHAT THE DIMENSION LOCATION IS.

FIGURE 1
ELEVATION OF CATHETER WITH NEW INDICIA SYSTEM
NTS

CATHETER CIRCUMFERENTIAL NUMBERING SYSTEM

5. INDICIA (#cm FROM TIP) TO BE EVERY CENTIMETER; EACH INDICIA TO BE PRINTED TWICE, ON OPPOSING FACES OF CATHETER/PROBE (= 180 deg FROM EACH OTHER) ("a")

6. EACH ADDITIONAL CENTIMETER INDICIA LOCATION TO BE ROTATED 90deg ("b")

PLAN OF CATHETER WITH NEW INDICIA SYSTEM
NTS

CATHETER CIRCUMFERENTIAL NUMBERING SYSTEM

PARTIAL AXONOMETRIC OF CATHETER WITH NEW INDICIA SYSTEM
NTS

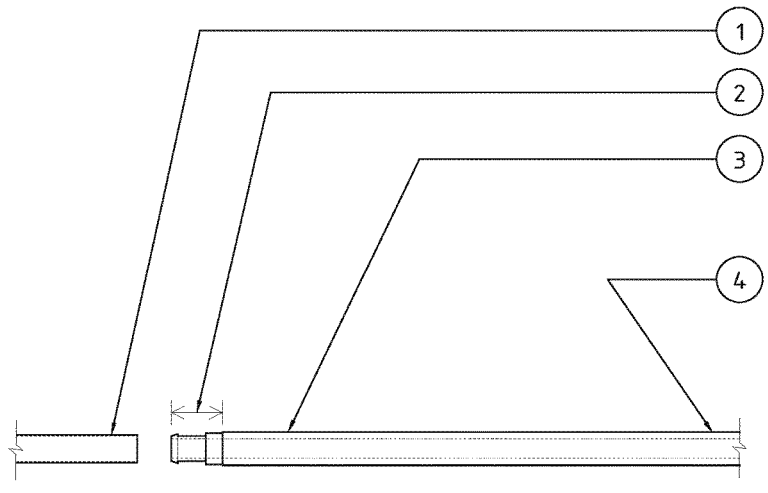

FIGURE 4a
PLAN & ELEVATION OF ANCHOR DRAIN NOT YET CONNECTED TO TUBING EXITING BODY

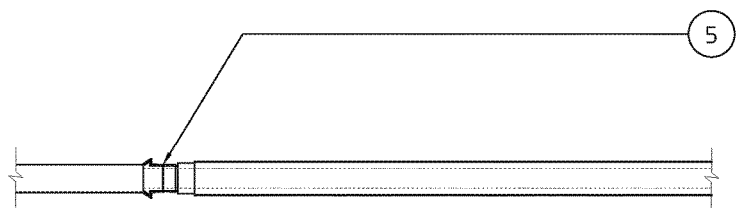

FIGURE 4b
PLAN OF ANCHOR DRAIN CONNECTED TO TUBING EXITING BODY

ANCHOR DRAIN– BASIC

1. "FIRST COMPONENT" TUBING WITH DRAIN HOLES SET WITHIN THE BODY, EXITING THROUGH THE SKIN. THIS TUBING SLIPS OVER THE PROFILED, MACHINED PIECE PROJECTING FROM THE ANCHOR DRAIN. THIS TUBING CAN BE AFFIXED WITH A SUTURE/TIE.
2. PROFILED, MACHINED PIECE PROJECTING FROM THE ANCHOR DRAIN TO PREVENT PULLOUT OF TUBING OF FIRST COMPONENT AND PREVENT OCCLUDING OF DRAIN TUBING.
3. *ANCHOR DRAIN* (SECOND COMPONENT)
4. TUBING TO DRAIN EXUDATE TO COLLECTION RECEPTACLE.
5. SUTURE TO SECURE TUBING FROM BODY ONTO ANCHOR DRAIN, AND TIE WITH SUTURE TO BODY. MACHINE END PREVENTS OCCLUDING OF LUMEN OF TUBE.

ANCHOR DRAIN-FLANGED_1 (NARROW)

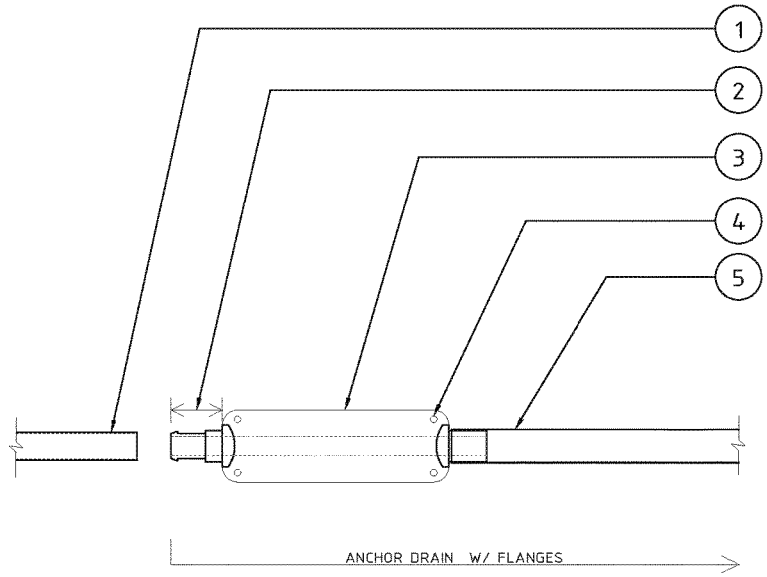

FIGURE 5a
PLAN OF ANCHOR DRAIN NOT YET CONNECTED TO TUBING EXITING BODY

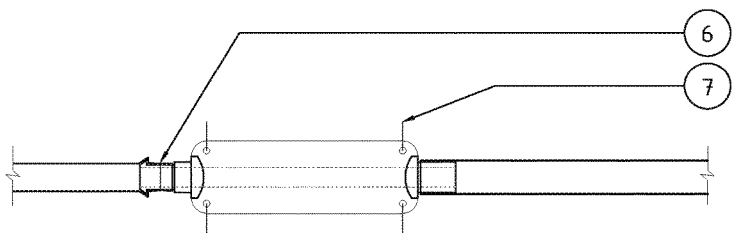

FIGURE 5b
PLAN OF ANCHOR DRAIN CONNECTED TO TUBING EXITING BODY

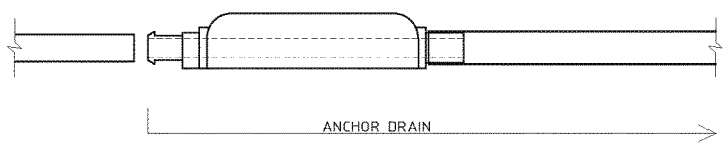

FIGURE 5c
ELEVATION OF ANCHOR DRAIN

1. "FIRST COMPONENT" TUBING WITH DRAIN HOLES SET WITHIN THE BODY, EXITING THROUGH THE SKIN. THIS TUBING SLIPS OVER THE PROFILED, MACHINED PIECE PROJECTING FROM THE ANCHOR DRAIN. THIS TUBING CAN BE AFFIXED WITH A SUTURE/TIE.
2. PROFILED, MACHINED PIECE PROJECTING FROM THE ANCHOR DRAIN TO PREVENT PULLOUT OF TUBING OF FIRST COMPONENT AND PREVENT OCCLUDING OF DRAIN TUBING.
3. *ANCHOR DRAIN* WITH FLANGES.
4. PREMADE HOLES FOR ADDITIONAL SUTURES TO AFFIX TO THE BODY.
5. TUBING EXITING ANCHOR DRAIN (MACHINED ONTO DEVICE) DRAINING TO COLLECTION RECEPTACLE.
6. SUTURE TO SECURE TUBING FROM BODY ONTO ANCHOR DRAIN. MACHINE END PREVENTS OCCLUDING OF LUMEN OF TUBE.
7. SUTURES AT PREMADE HOLES TO SECURE THE DRAIN DEVICE TO THE BODY.

ANCHOR DRAIN-FLANGED_2 (WIDE)

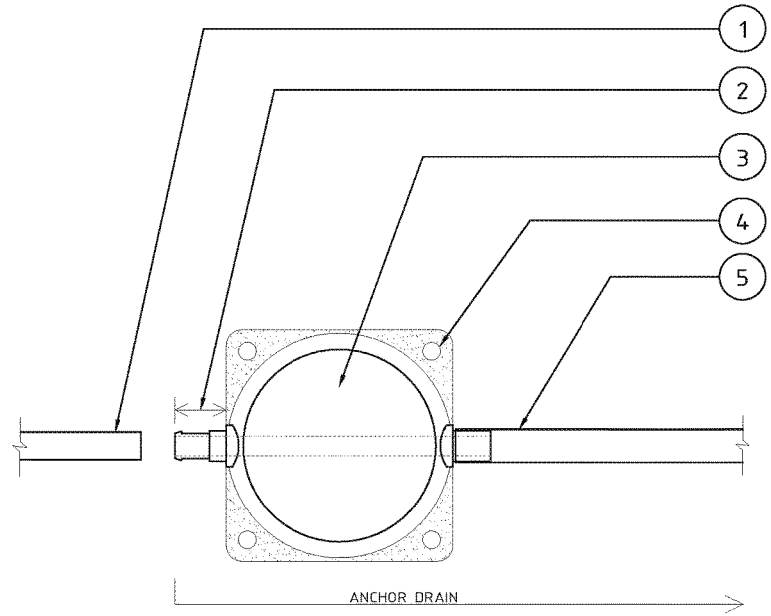

FIGURE 6a
PLAN OF ANCHOR DRAIN NOT YET CONNECTED TO TUBING EXITING BODY

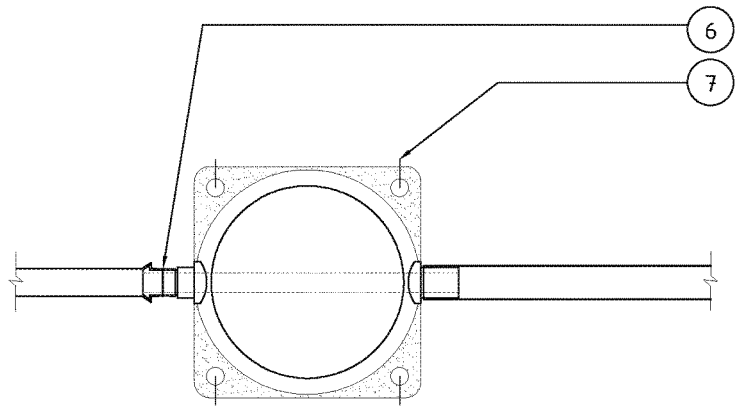

FIGURE 6b
PLAN OF ANCHOR DRAIN CONNECTED TO TUBING EXITING BODY

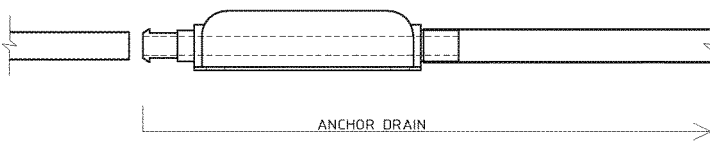

FIGURE 6c
ELEVATION OF ANCHOR DRAIN

1. "FIRST COMPONENT" TUBING WITH DRAIN HOLES SET WITHIN THE BODY, EXITING THROUGH THE SKIN. THIS TUBING SLIPS OVER THE PROFILED, MACHINED PIECE PROJECTING FROM THE ANCHOR DRAIN. THIS TUBING CAN BE AFFIXED WITH A SUTURE/TIE.
2. PROFILED, MACHINED PIECE PROJECTING FROM THE ANCHOR DRAIN TO PREVENT PULLOUT OF TUBING OF FIRST COMPONENT AND PREVENT OCCLUDING OF DRAIN TUBING.
3. *ANCHOR DRAIN* WITH WIDE FLANGES.
4. PREMADE HOLES FOR ADDITIONAL SUTURES TO AFFIX TO THE BODY.
5. TUBING EXITING ANCHOR DRAIN (MACHINED ONTO DEVICE) DRAINING TO COLLECTION RECEPTACLE.
6. SUTURE TO SECURE TUBING FROM BODY ONTO ANCHOR DRAIN. MACHINE END PREVENTS OCCLUDING OF LUMEN OF TUBE.
7. SUTURES AT PREMADE HOLES TO SECURE THE DRAIN DEVICE TO THE BODY.

CATHETER ANCHOR DRAIN

CROSS-REFERENCES TO RELATED APPLICATIONS

This application is entitled to priority to U.S. provisional patent application No. 62/108,123 filed 27 Jan. 2015.

BACKGROUND OF THE DISCLOSURE

The invention relates generally to the field of medical apparatus.

BRIEF SUMMARY OF THE DISCLOSURE

The disclosure relates to an improvement in an elongate medical device (e.g., a catheter) that is insertable into the body of a patient. The improvement includes a plurality of indicia (e.g., numerals, letters, or other symbols) borne by the device, each of the indicia representing a distance from the indicium to the distal end of the device. The indicia can, for example, be distributed circumferentially or helically about the long axis of the device. The indicia can be present in pairs (e.g., on opposite sides of the device), each indicium of a pair disposed equidistantly from the distal end of the device.

The disclosure also relates to an anchor drain for connecting a surgical drain having an outlet lumen to a fluid collection apparatus. The anchor drain has a body which includes a connection lug that is insertable within the outlet lumen of the surgical drain. The connection lug has a conduit extending therethrough to connect the outlet lumen of the surgical drain to an outlet defined by the body for connecting the body with the fluid collection apparatus. The connection lug also has a profiled outer surface (e.g., with one or more bulges or protrusions, such as a raised annular portion that surrounds the conduit at the end of the lug distal to the body) that resists disconnection of the surgical drain from the anchor drain. The connection lug preferably exhibits sufficient rigidity that it resists occlusion of the conduit when a suture is tied about a portion of the surgical drain into which the connection lug is inserted. In one embodiment, the anchor drain also includes a flange that bears a hole to facilitate suturing of the anchor drain to a surface of a patient bearing the surgical drain.

BRIEF SUMMARY OF THE SEVERAL VIEWS OF THE DRAWINGS

FIG. 1 is an elevation of a catheter bearing the circumferential numbering system described herein.

FIG. 4 consists of FIGS. 4A and 4B and illustrates aspects of the anchor drain described herein. FIG. 4A is a plan and elevation of the anchor drain, not yet connected to tubing exiting a patient's body.

FIG. 5 consists of FIGS. 5A, 5B, and 5C and illustrates aspects of an embodiment of the anchor drain described herein. FIG. 5A is a plan view of the anchor drain not yet connected to tubing exiting a patient's body. FIG. 5B is a plan view of the anchor drain connected to tubing exiting a patient's body. FIG. 5C is an elevation of the anchor drain.

FIG. 6 consists of FIGS. 6A, 6B, and 6C and illustrates aspects of another embodiment of the anchor drain described herein. FIG. 6A is a plan view of the anchor drain not yet connected to tubing exiting a patient's body. FIG. 6B is a plan view of the anchor drain connected to tubing exiting a patient's body. FIG. 6C is an elevation of the anchor drain.

DETAILED DESCRIPTION

Figure 2:
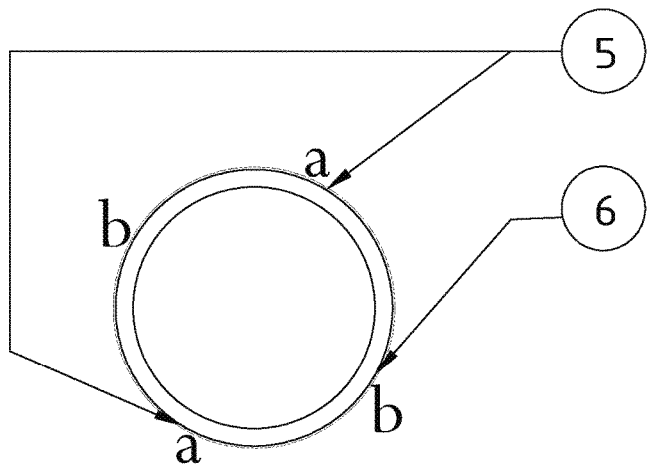
FIG. 2 is a cross section of the catheter illustrated in FIG. 1.

The disclosure relates to two distinct technologies, namely catheters bearing a helically-arranged, circumferential numbering system and an anchor drain for facilitating draining of fluid from a patient's body.

Part 1—Circumferential Numbering System for Catheters

This invention relates to the field of drains and catheters. For the purpose of this provisional patent application the invention is illustrated using ventricular catheters. More specifically, the invention offers an improvement to existing marking and measuring systems on the surface of the ventricular catheters and/or other long, narrow (i.e., elongate), minimally invasive medical devices which are inserted into the body via a small port.

Indicia on the surface of the catheter indicate the distance to the tip of the probe (i.e., the distal end, which is typically inserted first into the patient), measuring depth of catheter/probe within the body (brain).

The traditional method of indicating distance on a catheter is to include numerals or other indicia along the surface of the catheter, in a straight line, parallel to the shaft. Marks can be spaced regularly (i.e. every centimeter) or some sections can have more or fewer markings than others (i.e. every 5 centimeters or mostly every centimeter).

Additionally, some but not all catheters have markings with a corresponding number (i.e. marking what centimeter distance from the tip); these indicia and numerals have always been printed in a linear arrangement down the surface of the catheter at a substantially invariant circumferential position.

The surface material of a catheter is apt to rotate as it is advanced and/or secured. Traditional numerical systems are often difficult for the practitioner to see the indicia, requiring the practitioner to purposefully rotate and/or withdraw the catheter to find the next number or symbol, indicating depth. These maneuvers can compromise the location of the catheter, cause delays, and frustrate the practitioner, resulting in health and safety issues such as misplaced catheters and infection.

The present invention seeks to provide an improvement to the marking system of catheters, proposing a novel method of marking the indicia on catheters. Every marker is indicated firstly by a line circumscribing the shaft. This will occur at, for example, 4 cm, 5 cm, 6 cm, 7 cm, 8 cm, 9 cm and 10 cm from the tip of the shaft.

Each number (i.e. 4-10 cm) is printed preferably at least twice at each level, and this invention proposes that each adjacent mark are rotationally offset from one another about the circumference for example by 180 degrees (but could be another value such as 30, 60 or 90 degrees), rotated about the central axis of the shaft at each interval (i.e. cm) down the length of the catheter.

By rotating the numerals themselves in a double helical pattern around the surface of the catheter, the amount of probe within the body is simply and clearly legible regardless of how the catheter twists, without disturbing the placed catheter.

This indicia system could be used for plain ventricular catheters, antibiotic impregnated ventricular catheters, and/or any catheter or drain where a legible distance from an insertion point is required.

Part II—Anchor Drain

This invention relates to the field of post-operative or wound drain systems. More specifically, the invention offers an anchoring system to the skin which replaces current drainage systems that have no inherent anchor to the skin, resulting frequently in the premature and unintentional disconnection and/or removal of said drains.

There are many wound and post-surgical drainage devices. Most of these are temporarily and loosely secured to the body with tape (adhesive) and or suture. However, these methods of attachment are inadequate for preventing accidental disconnection and/or removal during wound dressing changes, during patient transfers, during early mobilization and physical therapy, during bathing and even sleeping.

A traditional drain consists of two elements—the first is a hollow tube with multiple openings at the proximal end, placed in the part or cavity of the body requiring drainage, interior to the body cavity which is then tunneled away from the incision line and exiting out through the skin, and then cut in preparation to connect to the second component; the second component loosely connects to the distal end of the first component (outside of the body) and ultimately is attached to a collecting apparatus that drains the cavity by either suction or gravity, per the recommendation of the treating physician.

Near where the first component exits the body, at the skin, current strategies for securing the drain system to the patient consist of placing adhesive tape around the drain to the patient's skin or placing a suture through the skin and tying it around the drain (either one tie or multiple ties at various locations along the drain, and with the drain tubing either in a straight line or in a spiral pattern) to increase the fixity and pullout strength of the system. This technique has severe limitations, mainly that if the suture is adequate to prevent pullout and provide stability of the system, it will occlude the lumen thereby rendering useless the drain. Tying the suture to avoid occluding the lumen results in an ineffectual (too loose) connection to the drain. Tape and other adhesives are even less effective than suturing because skin movement and/or moisture causes the adhesive to fatigue and fail.

Current techniques that provide adequate drainage do not provide sufficient security of the drain to the body, which can result in premature removal or dislocation of the drain. When this occurs, fluid that was meant to be removed will accumulate in that body cavity, leading to a myriad of complications including: infection, pain, emergent replacement (in the case of an externalized ventricular drain) or elective replacement, poor wound healing, and/or a prolonged hospital stay.

The present invention seeks to provide an adequate anchoring system without compromising the efficacy of the drainage system.

The present invention consists of a novel second component with an integral connecting and anchoring unit to connect to the distal end of the first component. The first component of the drainage system remains the same (a hollow tube with drainage holes at the proximal end, placed within the body and exiting through the skin). The novelty of this system is in the proximal end of the second component. The second component will now consist of a male end with an integral, machined, MRI compatible, metal (or hard plastic) conduit which resists disconnection from attached tubing (e.g., cannot be disconnected from its tubing easily or at all), and resists occlusion (e.g., cannot be occluded by a suture tied with ordinary human strength) when suturing the tubing to the skin. The male end (proximal portion of the second component) is inserted into the female end (distal portion of the first component). The female end of the first component is cut at or near the exit point through the skin. The male end inserts into the female end at or near the skin edge and a suture is used to not only firmly connect the two (male and female) components so they do not uncouple, but also to strongly anchor the drainage tubing to the skin.

A single suture is all that is required to connect the male and female components of the drainage system and at the same time securely anchor the system to the patient's skin without compromising the lumen of the drainage system. The male component is a fixed length and can be connected to a suction device such as a hemovac or bulb suction at the factory or it can be assembled in the field. In the case of a ventricular catheter the distal end of the male component can have the drainage tubing connector attached at the factory or assembled in the field. The first component (proximal end in the body cavity requiring drainage) will have indicia markings and will require cutting at the point where the catheter exits the skin creating the female end and allowing coupling of the male and female components at or near the exit site through the skin.

The connection between the first and second components would be quickly, safely and easily secured by placing the male end of the novel anchor into the female end of the first component of the drain—at or very near the exit site at the skin. Because of the extreme rigidity of the male component, once the female end of the tubing is placed over it, a suture can be tied around the entire system, guaranteeing two things: a substantially stronger system than currently exists in terms of disconnection and pull-out strength, and in ensuring a patent lumen.

Improvements of this BASIC ANCHOR DRAIN include the addition of flanges on or near the male end of the second component, with integral holes, allowing for multiple attachment sites with sutures, further augmenting the pullout strength of the drainage system from the body. There would be an array of sizes of the male end to accommodate the diameters of different drains/lumens.

A skilled artisan in this field appreciates the materials from which the devices described herein can be made, as well as methods of making such devices.

Examples

The subject matter of this disclosure is now described with reference to the following Examples. These Examples are provided for the purpose of illustration only, and the subject matter is not limited to these Examples, but rather encompasses all variations which are evident as a result of the teaching provided herein.

Figure 3:
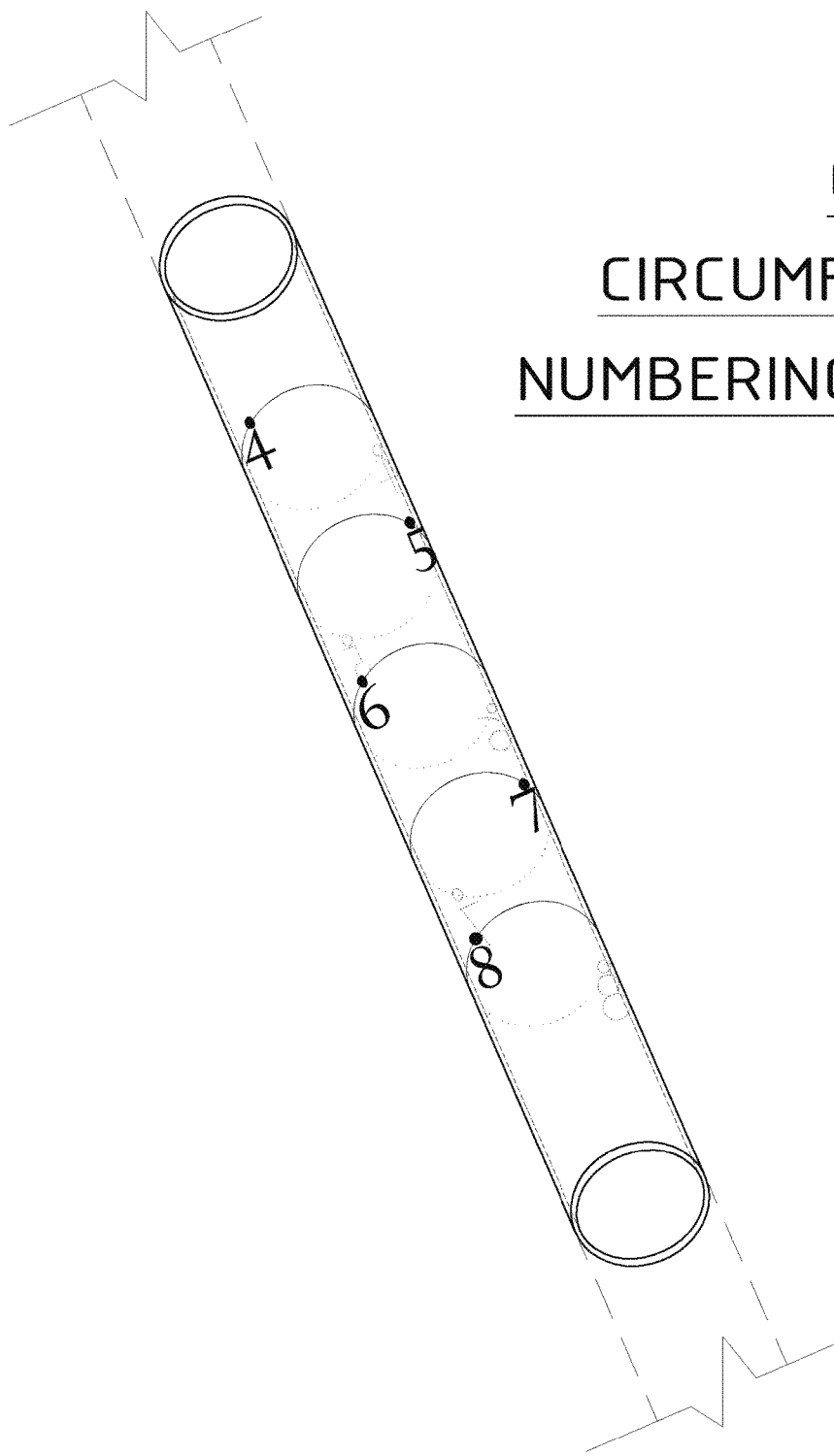
FIG. 3 is a partial axonometric of the catheter illustrated in FIG. 1.

Examples of the catheter numbering system are illustrated in FIGS. 1-3.

Examples of the anchor drain are illustrated in FIGS. 4-6.

The disclosure of every patent, patent application, and publication cited herein is hereby incorporated herein by reference in its entirety.

While this subject matter has been disclosed with reference to specific embodiments, it is apparent that other embodiments and variations can be devised by others skilled in the art without departing from the true spirit and scope of the subject matter described herein. The appended claims include all such embodiments and equivalent variations.

What is claimed is:

1. An anchor drain for connecting a surgical drain to a fluid collection apparatus, the surgical drain comprising an outlet lumen and a ventricular catheter, the anchor drain comprising:

a body which comprises a connection lug outside the body of a patient, the connection lug is insertable within the outlet lumen of the surgical drain exiting out through skin of the patient, the connection lug having a conduit extending therethrough to connect the outlet lumen of the surgical drain to an outlet defined by the body for connecting the body with the fluid collection apparatus, the connection lug comprising a profiled outer surface that (i) comprises a raised portion at the end of the connection lug distal to the body and insertable within the outlet lumen of the surgical drain and (ii) that resists disconnection of the surgical drain from the anchor drain wherein the connection lug exhibits sufficient rigidity to resist occlusion of the conduit wherein a suture is tied about a portion of the surgical drain where the connection lug is insertable to prevent pull-out, wherein the suture is configured to be tied to the skin of the patient to securely anchor the anchor drain to the patient's skin.

2. The anchor drain of claim 1, wherein the connection lug bears a bulging profile at the portion of the lug that is insertable within the outlet lumen of the surgical drain.

3. The anchor drain of claim 2, wherein the connection lug bears an annularly-bulging profile at the portion of the lug that is insertable within the outlet lumen of the surgical drain.

4. The anchor drain of claim 1, wherein the body further comprises a flange that bears a hole to facilitate suturing of the anchor drain to a surface of a patient bearing the surgical drain.

* * * * *